(12) United States Patent (10) Patent No.: US 7,933,379 B2
Grodzins et al. (45) Date of Patent: *Apr. 26, 2011

(54) MEASUREMENT OF LEAD BY X-RAY FLUORESCENCE

(75) Inventors: Lee Grodzins, Lexington, MA (US); John Pesce, Melrose, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/726,306

(22) Filed: Mar. 17, 2010

(65) Prior Publication Data

US 2010/0189215 A1    Jul. 29, 2010

Related U.S. Application Data

(63) Continuation of application No. 12/205,678, filed on Sep. 5, 2008, now Pat. No. 7,702,067.

(60) Provisional application No. 60/967,722, filed on Sep. 6, 2007.

(51) Int. Cl.
*G01N 23/223* (2006.01)
(52) U.S. Cl. .................................................. 378/45
(58) Field of Classification Search .......... 378/44–50
See application file for complete search history.

(56) References Cited

U.S. PATENT DOCUMENTS 7,702,067 B2 * 4/2010 Grodzins et al. ............. 378/45

\* cited by examiner

*Primary Examiner* — Jurie Yun
(74) *Attorney, Agent, or Firm* — Charles B. Katz

(57) ABSTRACT

A method, instrument, and computer program software product for characterizing a sample with respect to the presence of a specified element, either as a constituent of a surface layer or of the bulk of the sample. Intensities of fluorescent emission at two characteristic emission lines are compared to establish whether the specified element is disposed above the bulk of the sample. In the case where the specified element is disposed above the bulk of the sample, an areal density of the specified element is determined, whereas in the case where the specified element is disposed within the bulk of the sample, a volumetric concentration of the specified element within the sample is determined.

7 Claims, 5 Drawing Sheets

MEASUREMENT OF LEAD BY X-RAY FLUORESCENCE

CROSS-REFERENCE TO RELATED APPLICATIONS

The present application is a continuation under 35 U.S.C. §120 and claims the priority benefit of U.S. patent application Ser. No. 12/205,678, filed Sep. 5, 2008, now U.S. Pat. No. 7,702,067, which claims the priority benefit of U.S. Provisional Patent Application Ser. No. 60/967,722, filed Sep. 6, 2007. The disclosures of each of the foregoing applications are incorporated herein by reference.

TECHNICAL FIELD

The present invention relates to methods for determining the concentration of a specified elemental substance employing x-ray fluorescence techniques, and, more particularly, to methods for determining elemental concentrations based on identifying whether the specified substance is a paint-like outer layer or is admixed with the bulk sample or is buried under a layer of non-leaded material.

BACKGROUND ART

Lead has been known to be a toxic element for more than a century. It is especially harmful to children, producing severe adverse effects to their mental and behavioral abilities in direct proportion to the concentration level of lead in their bodies. Governments have limited the concentration of lead in paint and in bulk materials in order to protect the safety of the public, prevent the build up of toxic elements in waste disposals and prevent its reuse in recycling.

Prior teachings of techniques for measuring concentrations of lead in surface-covering layers, such as paint, even when subsequently covered by layers of non-lead paint of unknown thickness and composition, may be found with reference to the following patents: U.S. Pat. Nos. 5,274,688, 5,390,229, and 5,396,529 (all, to Grodzins, and collectively, "Grodzins"), all entitled "Lead Paint Detector," teach measurement of the concentration of lead in paint on the basis of inducing and detecting fluorescence of the L x-rays of lead. U.S. Pat. No. 5,461,654 (to Grodzins and Parsons, and referred to, hereinafter, as "Grodzins/Parsons"), entitled "X-ray Fluorescence Detector," teaches a method that provides a measure of the depth of a layer of lead paint beneath one or more layers of paint from which lead is absent. The disclosures of all of the foregoing Grodzins and Grodzins/Parsons patents are incorporated herein by reference. Layer depth, in the prior art, is measured in attenuation units of gm/cm$^2$ and gives no measure of either the density or the elemental composition of the overlayers of paint.

There is an urgent need, unmet by prior techniques, to distinguish, automatically and non-destructively, between toxic elements in a surface layer on an object, possibly buried beneath other material, and similar elements that form one or more constituents of the object's bulk. The distinction must be made if quantitative results are to be obtained.

SUMMARY OF THE INVENTION

In accordance with embodiments of the present invention, methods are provided for determining a concentration of elements in a sample by techniques of x-ray fluorescence (XRF). A method is described for automatically distinguishing whether toxic elements are on the surface of the sample, in the form, for example, of paint or veneer, or whether such elements are distributed throughout the bulk of the sample, or whether the lead is buried beneath unleaded material. The distinction is then used to automatically select the appropriate algorithm for quantitative measurement by a thin film mode of analysis or a bulk sample mode of analysis, or a buried layer mode. If the element is part of the surface layer, or in a buried layer, the concentration is presented in units of grams per square centimeter. If the element is part of the bulk, the XRF spectrum is used to automatically obtain a quantitative measure of the density of the bulk material so that the concentration can be presented in units of grams of analyte per gram of the bulk. In accordance with certain embodiments of the methods described, the presence of lead in toys may be determined.

In accordance with preferred embodiments of the present invention, a method is provided for characterizing a sample with respect to the presence of a specified element. The method has steps of:

a. illuminating a surface of the sample with x-ray excitation radiation;

b. measuring a first intensity of a characteristic emission line of the specified element at a first energy;

c. measuring a second intensity of a characteristic emission line of the specified element at a second energy;

d. comparing the first intensity to the second intensity to establish whether the specified element is disposed above the bulk of the sample;

e. in the case where the specified element is disposed above the bulk of the sample, determining an areal density of the specified element; and f. in the case where the specified element is within the bulk of the sample, determining a volumetric concentration of the specified element within the sample; and g. outputting at least one of the areal density and volumetric concentration of the specified element.

In accordance with other embodiments of the invention, in the case where the specified element is disposed above the bulk of the sample, the method may have a further step of comparing the first intensity to the second intensity to establish whether the specified element is contained within a buried layer. The first and second characteristic emission lines of the specified element may be $L_\alpha$ and $L_\beta$ emission lines of the specified element, and the specified element may be lead, in particular. The specified element may also be selected from the group of light elements including barium, cadmium and arsenic, and the first and second characteristic emission lines of the specified element may be $K_\alpha$ and $K_\beta$ emission lines of the specified element. Alternatively, the specified element may be selected from the group of heavy elements including mercury, lead, and uranium, and the first and second characteristic emission lines of the specified element are $K_\alpha$ and $K_\beta$ emission lines of the specified element. A ratio of first and second emission line intensities equal to an empirically determined minimum may signify presence of the specified element outside the bulk of the sample.

The method may also include measuring Compton scattering of fluorescence lines in the bulk of the sample for determining absorption in the sample as a function of x-ray energy.

In accordance with another aspect of the present invention, an x-ray fluorescence spectrometer is provided for determining a concentration of a specified element. The spectrometer has a source of x-ray excitation for illuminating a surface of a sample and a detector for measuring a first intensity of a first characteristic emission line of the specified element at a first energy and a second intensity of a second characteristic emission line of the specified element at a second energy, and for outputting a detector signal corresponding to each of the first and second intensities. The spectrometer also has a signal processor for comparing the first intensity to the second intensity to establish whether the specified element is disposed solely on the surface of the sample. Finally, the spectrometer has an output for providing an areal density of the specified element in the case where the specified element is disposed solely on the surface of the sample, and for outputting a volumetric concentration of the specified element within the sample in the case where the specified element is not disposed solely on the surface of the sample.

In accordance with yet another aspect of the invention, a computer program product is provided for use on a computer system for characterizing a sample with respect to the presence of a specified element. The computer program product has a computer usable medium having computer readable program code thereon, the computer readable program code including:

a. a module for receiving a first intensity of a characteristic emission line of the specified element at a first energy;
b. a module for receiving a second intensity of a characteristic emission line of the specified element at a second energy;
c. a module for comparing the first intensity to the second intensity to establish whether the specified element is disposed above the bulk of the sample;
d. a module for
   in the case where the specified element is disposed above the bulk of the sample, determining an areal density of the specified element, and
   in the case where the specified element is not disposed above the bulk of the sample, determining a volumetric concentration of the specified element within the sample; and
e. a module for outputting at least one of the areal density and volumetric concentration of the specified element.

The computer program product may also have a module for determining absorption in the sample as a function of x-ray energy.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

In accordance with preferred embodiments of the present invention, rapid and effective ways are provided to use an x-ray fluorescence (XRF) spectrum in order to distinguish automatically between surface and bulk concentrations and to use the fluorescence spectrum obtained to determine the essential parameters for a quantitative value for the concentration in bulk samples.

As used herein and in any appended claims, the term "areal density" refers to the volume density of an element integrated along a line of sight to a depth to which the measurement is effectively made; for material of uniform density and thickness, the areal density is simply the density multiplied by the sample thickness. Areal density is typically expressed in units of mass per unit area, such as g/cm².

The methods of the present invention are described, without limitation, with reference to data obtained using the handheld Niton XL3, sold by ThermoFisher Scientific. This XRF spectrometer, discussed by way of example, uses a controllable x-ray tube to produce an appropriate x-ray excitation beam, a sensitive SiPIN diode to measure the intensity of fluoresced x-rays as a function of the x-ray energy and an appropriate pulse processor and computer to analyze the detected pulses of fluoresced x-rays and determine the concentration of the detected elements.

The method of the present invention is described herein in terms of the measurement of lead in toys, although it is to be understood that such application of the method is provided solely by way of example, and that the method is applicable in many other circumstances. It will be readily apparent to persons of ordinary skill in the art that the methods taught herein may be applied to a wide variety of elements in a wide variety of products. The measurement of lead in toys, however, is a ubiquitous problem of international concern. The toy industry has special responsibilities since children put the toys in their mouths, chew on them, and occasionally swallow parts.

Painted toys do not have more than a few coats of paint, each typically no thicker than 0.05 mm, and the paint is put on during production of the toy. Toys are generally made of light materials such as plastics or elastomers whose major elements are hydrogen, carbon, nitrogen and oxygen. The specific density of the materials employed is typically close to unity (i.e., one), the main exception being metal parts.

The concentration of lead in a surface layer, such as a paint or a veneer, is typically measured in units of mass per unit surface area, for example, in grams of lead per square cm of surface area. Regulations are generally given in units of milligrams per square cm; i.e. mg/cm². The concentration of lead in bulk material, on the other hand, is typically measured in grams of lead per gram of the bulk material. Regulations are generally given in micrograms of lead per gram of material; i.e. µg/g, which is often written as ppm (parts per million).

Figures 1A, 1B, 1C:
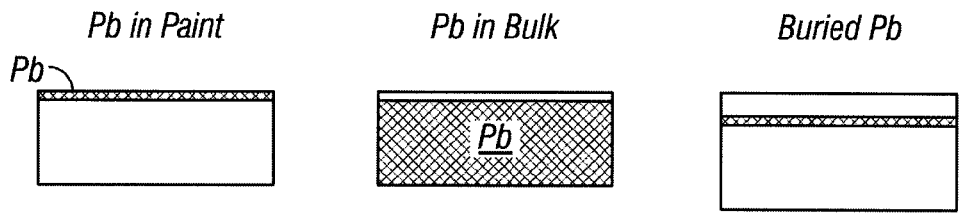
FIG. 1A depicts an object that is free of lead in its bulk, but that is painted with a surface layer of paint containing lead.
FIG. 1B depicts an object, the painted surface of which is free of lead, but which itself contains lead as a constituent.
FIG. 1C depicts an object in which a layer containing lead lies beneath material that is free of lead, for example, a layer of lead-containing paint sandwiched beneath paint or veneer that does not contain lead. The bulk material is also lead-free.
Figure 2A:
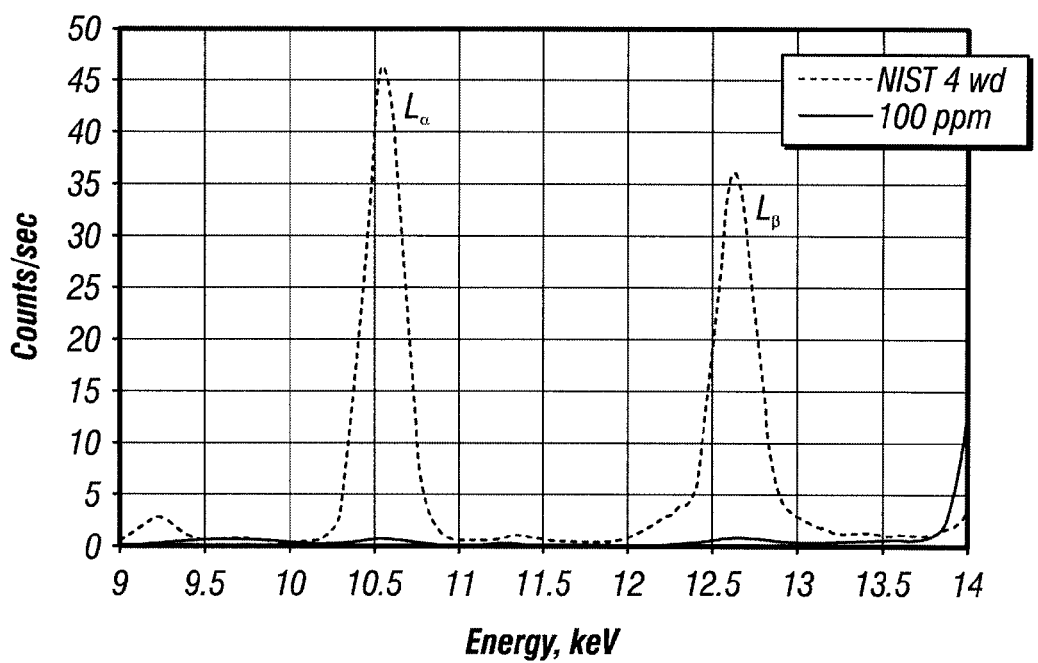
FIG. 2A shows XRF spectra of 330 µg/cm² of Pb in lead paint on the surface of lead-free wood, and 100 µg/g of lead in thick gypsum. The strength of the lead peaks at 10.5 keV and 12.6 keV are 50 and 30 times, respectively, smaller in the case of the lead within the volume of gypsum than in the case of the painted wood.
Figure 2B:
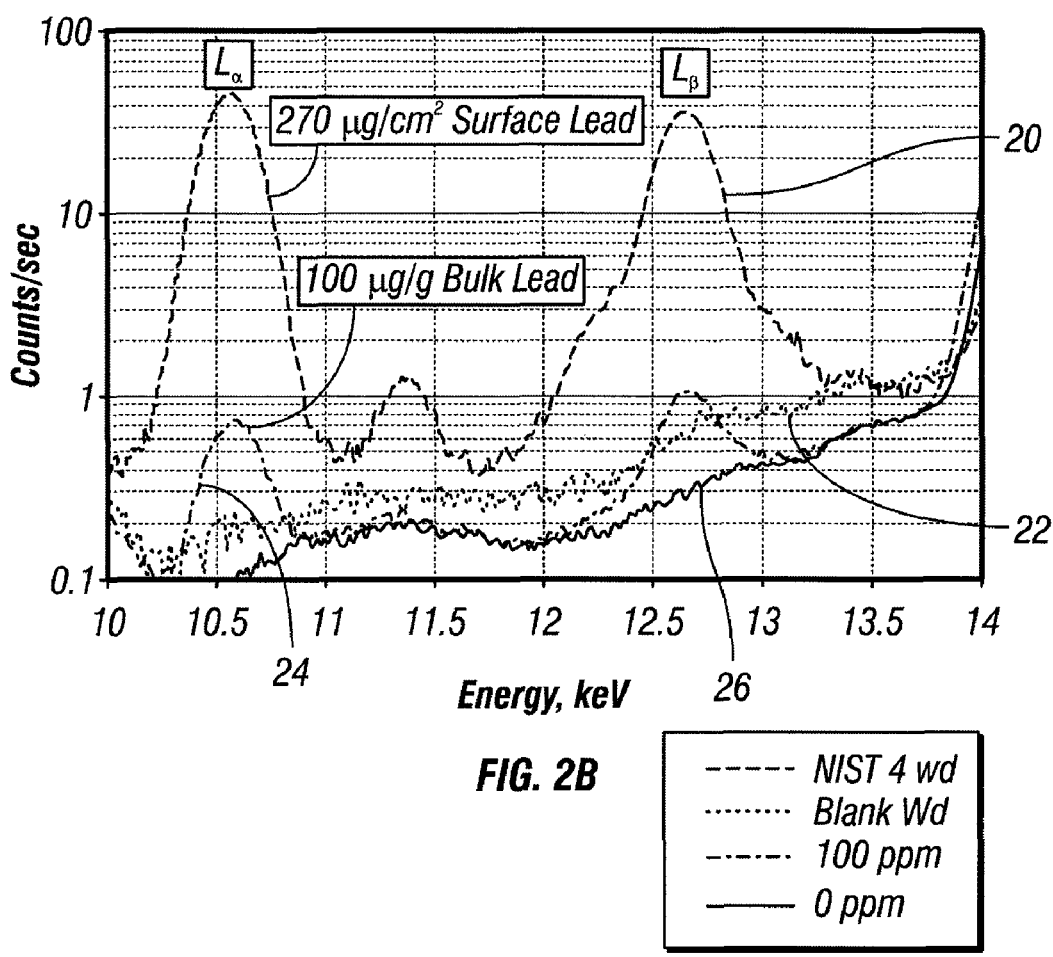
FIG. 2B shows the same spectra as in FIG. 2A, but the intensity scale is logarithmic rather than linear in order to show the background spectra in the two cases and to emphasize the dramatic difference in the $L_\beta/L_\alpha$ ratio.

While the description below posits current United States regulations that limit lead concentration in any toy material to less than 600 µg/g, that regulation is in flux. In particular, a separate regulation will be provided for the paint on toys in terms of μg/cm². It is not possible to determine by visible inspection whether the lead detected by the XRF instrument is present in surface paint or in the bulk material, or is buried in a layer underlying the surface paint and overlying the bulk material. Moreover, each of these situations, shown in FIGS. 1A, 1B, and 1C, requires a different analytic algorithm. If the wrong algorithm is used, a toy may be found to be out of compliance with regulations when in fact it is in compliance and vice versa. FIGS. 2A and 2B illustrate this essential point.

FIG. 2A shows the spectra in the lead L x-ray region for two samples: The large double-peak spectrum, one peak centered at 10.5 keV and the other at 12.6 keV, is the spectrum of a paint layer of 330 μg/cm² on wood. The lower double-peak spectrum (less intense by more a factor almost 50) is of a polyethylene sample containing 100 μg/g of lead. FIG. 2B shows the intensities of the same two spectra in log form, together with background spectra obtained from samples of the same materials but free of lead. The polyethylene sample, with a bulk concentration of 100 μg/g, was 1 cm thick so its areal density of lead was 100 μg/cm².

The measured count rates in the two spectra differ by a factor of about 50. In terms of areal densities, the two spectra only differed by a factor of 3.3; that is, 330 μg/cm² to 100 μg/cm². If, on the other hand, the two spectra are compared in terms of parts per million, the difference is just as striking. The 330 μg/cm² paint layer was thin, its mass per square centimeter was 10 mg/cm². The paint layer, therefore, had a lead concentration of 33,000 μg/g. The paint layer is in compliance in terms of μg/cm² and completely out of compliance if measured in terms of μg.

Embodiments of the current invention automatically distinguish surface lead from both bulk lead and buried lead. As further discussed below, surface lead or a buried layer of leaded material, is measured directly in terms of μg/cm², without needing any further information about the sample. A quantitative measurement of lead in bulk, however, requires some knowledge of the thickness of the bulk material.

The invented method described herein accomplishes several important new functions and does so automatically without the need for any input by the operator of the inspection instrument, otherwise referred to herein as the inspector. In the detailed description that follows, steps of the method are presented using the non-limiting example of the detection of lead in toys.

Methods in accordance with the present invention are described with reference to the three, lead-containing objects of FIGS. 1A-C. In FIG. 1A, the lead is in the paint on the surface. In FIG. 1B, the lead is distributed throughout the bulk. In FIG. 1C, the lead is in a buried layer sandwiched between a non-leaded outer layer and a non-leaded bulk.

The objectives of distinguishing surface lead (also referred to herein, as "above the bulk") versus bulk lead, and of further determining thicknesses and densities are best illustrated with an example. Assume the paint in FIG. 1A contains 300 μg of lead in each square centimeter. This lead paint is in compliance with U.S. EPA regulations requiring that the lead concentration for lead in painted walls be less than 1000 μg/cm². If, however, the 300 μg of lead is distributed uniformly in the bulk, as in FIG. 1B, then the concentration of lead in each square centimeter measured in μg/g will depend on both the thickness and density of the bulk material that is measured.

For example:

If the density of the bulk is 1 gm/cm³, and the thickness is one centimeter, then the lead concentration is 300 μg. This concentration is only half of the 600 μg/g regulatory limit based on the regulation that has long been in place for toys but that will be reduced over the course of the next few years. The material is, thus, in compliance.

If the same material is only 2.5 mm thick, the concentration rises to 1,200 μg/g; that is 300 μg divided by a volume of 0.25 cm³. The material is no longer in compliance.

If the bulk material is aluminum, with a density of 2.7, then a 1 cm thick sample has a lead concentration of 111 μg/g of lead, and is in compliance even if it is only 2.5 mm thick.

Thus, a determination as to whether an article is in regulatory compliance requires knowledge of the lead distribution and the effective thickness of the lead containing material.

In accordance with preferred embodiments of the present invention, the ratio of the intensity of two characteristic lines of a specified element is used to distinguish the three situations depicted in FIGS. 1A, 1B and 1C so that the proper algorithms can be used to give correct concentration values.

a. The $L_\alpha$ line at 10.5 keV and the $L_\beta$ line at 12.6 keV are the appropriate signature lines to measure the concentration of lead.
b. In general the L lines of an element are appropriate signature lines for the application of the method to the measurement of the concentration of all heavy elements, including mercury and uranium.
c. For lighter elements, such as barium, cadmium, and arsenic, the $K_a$ and $K_b$ lines may be used if their intensities can be measured.

After identifying that the lead is present in the bulk material, the ratio of the intensities of the L lines is used to determine the areal density of bulk material that is contributing to the intensity of the L lines.

The XRF spectrum, in particular the intensity of the fluoresced spectrum due to the Compton effect and the presence of significant amounts of heavier elements, gives a good measure of the absorption coefficient of the bulk material as a function of the energy of the x-rays.

The intensities of the L lines of lead together with the absorption coefficients for the relevant x-rays, allows the concentration of lead to be given in micrograms of lead per gram of material.

In principle, the ratio of quantitative values for obtaining either surface lead or bulk lead can be obtained by analytic methods alone but this requires a detailed knowledge of geometrical factors, detector efficiencies, fluorescing spectra, etc. In practice, the relevant values that depend on these factors are determined at the factory using standards with know concentrations of lead at the surface and in the bulk.

Distinguishing Surface Lead from Bulk Lead

Figure 3:
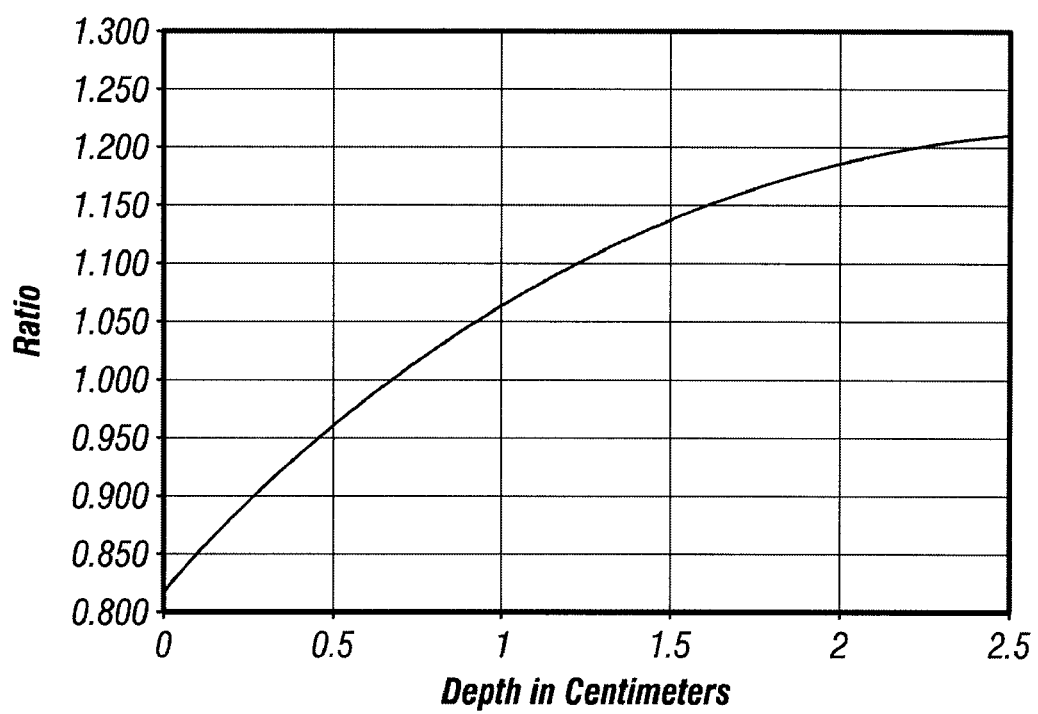
FIG. 3 is a theoretical plot of the ratio of the $L_\beta$ to $L_\alpha$ intensities of lead as a function of the thickness or areal density of the material that contains the lead; geometrical effects on the ratio have been ignored

Methods of distinguishing surface lead from bulk lead are described with reference to FIGS. 2 and 3.

FIG. 2A shows the x-ray spectra, from 8 keV to 16 keV, from surface lead and bulk lead. The prominent spectrum, and the only one fully visible at the intensity scale of the figure, is that of a NIST IV lead-paint calibration card containing 300 μg of lead per cm². The card is backed with 2 cm of wood. The two strong peaks are the $L_\alpha$ line at 10.55 keV and the $L_\beta$ line at 12.61 keV. The $L_\alpha$ line is 18% stronger than the $L_\beta$ line. Both intensities are about 100 times the intensity of the background under the respective lines. These two peaks are the signature lines that identify the presence of lead.

If the 300 μg of lead per square centimeter were extended uniformly through the bulk of a thick material, then the concentration of lead in 300 μg will depend on the density of the material and the depth of measurement. In any case, the XRF spectrum would change. This fact is illustrated in FIG. 2B, which shows FIG. 2B in log form to expose four spectra. Those spectra are the following:

1. The intense spectrum 20 from the surface lead.
2. The background spectrum 22 for the surface lead obtained by substituting a NIST null calibration for the NIST IV lead calibrator.
3. The spectrum 24 obtained from a lead-in-bone calibration standard made from gypsum, with 100 µg/g of lead.
4. The background spectrum 26 obtained from a null gypsum standard is the lowest spectrum in the figure.

The density of the gypsum is 2.3 g/cm$^3$ so there is 233 µg of lead per cubic centimeter of sample; i.e. 100 µg×2.3 g/cm$^3$. If the lead were on the surface of a 1 cm thick gypsum sample, its concentration would be 230 µg/cm$^2$, 70% of the lead value in the NIST IV sample.

Attention is directed to three striking differences between the spectra of the surface lead 20 and the bulk lead 24, both taken with the same Niton XL3 analyzer.

1. The count rates of the L lines from the surface lead are 50 times greater than those from bulk lead. If the bulk lead spectrum were analyzed as surface lead, the concentration would be grossly in error.
2. The intensity of the L lines from surface lead is more than 50 times the background under the peaks. For the denser bulk material, with the same order of magnitude of lead, the L lines are, at most, a few times the background.
3. The $L_\beta/L_\alpha$ ratio for surface lead is 0.8; i.e., less than unity. The ratio for bulk lead is 1.26. This change in the $L_\beta/L_\alpha$ ratio is the differentiator of surface and bulk lead.
4. Strength of the L lines for lead in bulk depends strongly on the presence of heavy elements, such as calcium in the case of gypsum. The $L_\beta/L_\alpha$ ratio is almost independent of composition of the bulk material.
5. The reversal in the $L_\beta/L_\alpha$ ratio with thickness is almost independent of the composition of the materials.

Figure 5:
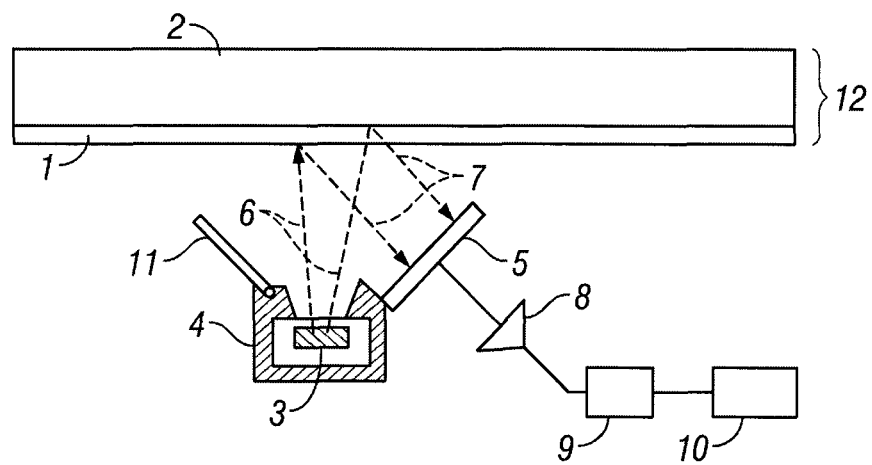
FIG. 5 is a schematic view of an instrument that may be used in practice of methods that are within the scope of the present invention.
Figure 6:
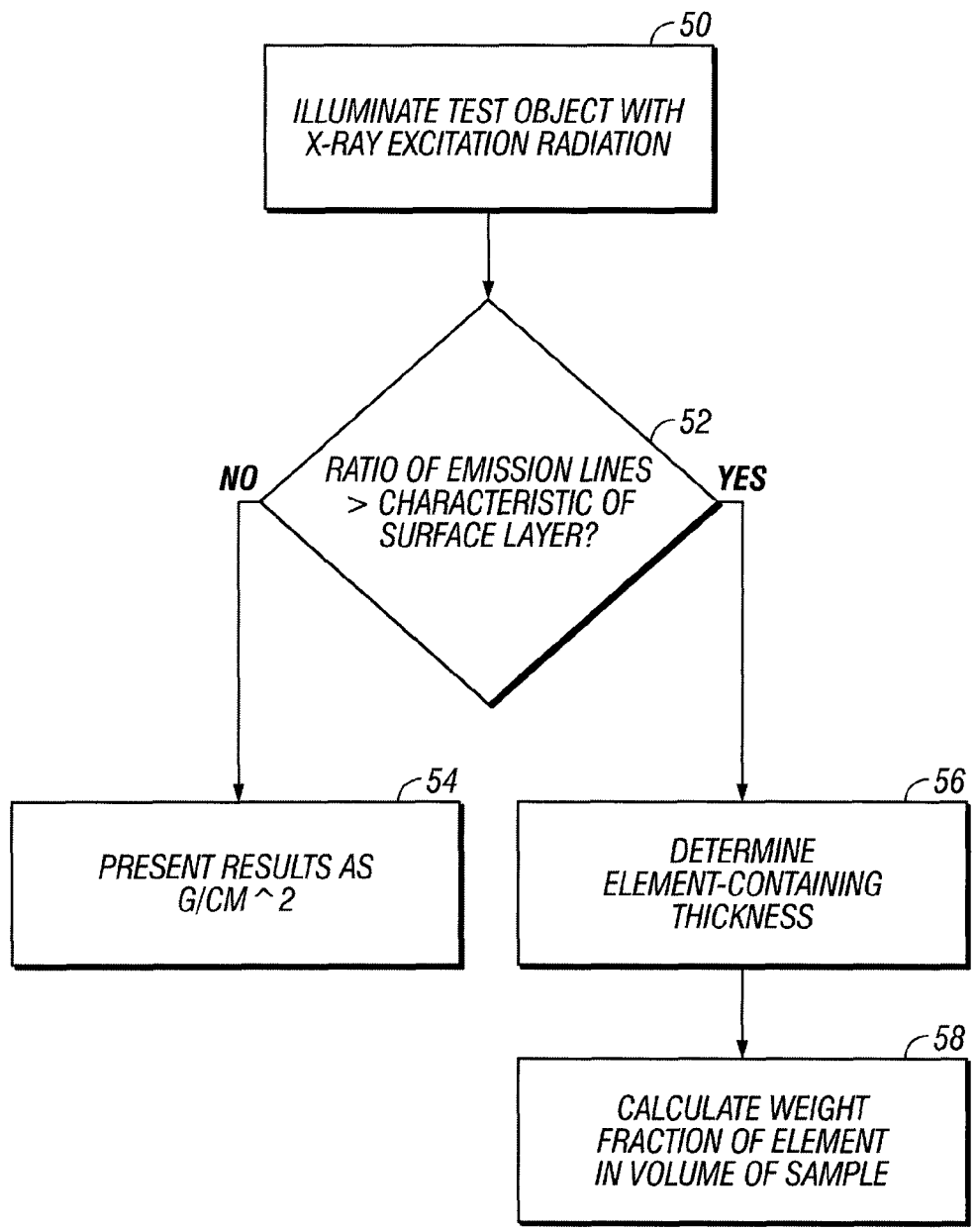
FIG. 6 is a flowchart depicting steps of a method in accordance with an embodiment of the present invention.

Analytic Steps to Measuring the Concentration of a Specified Element, such as Lead An instrument which may be applied to perform methods of the present invention is depicted in FIG. 5. A source 3 emits initiating photons 6 that, with the safety cover 11 off, impinge on test object 12 that consists of a surface layer 1 of material such as coats of paint, that is on a substratum 2 of material such as wood. The detector 5 detects a spectrum of photons 7 that consist of fluorescent x-rays, and photons from the initiating source that are scattered by the sample 12. A shield 4 isolates the detector 5 from the direct radiations from the source 3. The signals from the detector 5 are amplified by amplifier 8, processed by an appropriate signal processor 9 and the results presented in the appropriate output 10.

Referring to the flowchart of FIG. 5, x-ray photons emitted by source 3 are used, in step 50, to illuminate sample 12 and to initiate fluorescent emission. The ratio of intensities measured in the two fluorescence emission lines, such as the $L_\beta/L_\alpha$ ratio, is used, in step 52, to determine whether the lead is on the surface of the object or is a constituent of the object. If the ratio is that expected for surface lead, the data are analyzed 54 on that assumption and present the results in g/cm$^2$.

If the ratio is greater than the ratio expected for surface lead, the measured ratio is used 56 to determine the thickness of material that contains the lead and analyze 58 the data in the bulk mode.

Eq. 1a gives the relationship between the intensity of the $L_\alpha$ peak, the mass absorption coefficients, $\mu(E_{in})$, $\mu(L_\alpha)$, $\mu(p.e)$, for, respectively, the fluorescing radiation, the $L_\alpha$ line, and the photoelectric mass absorption coefficient resulting in the emission of an $L_\alpha$ x-ray. D is the areal density, in g/cm$^2$, of the sample in which the lead is uniformly distributed and f is the weight fraction of the lead in the material. The quantity C contains factors such as geometrical and detection efficiencies. The geometrical efficiencies are assumed here to be constant, which, for a thick sample, is only a good approximation if the sample is far from the x-ray source and detector.

$$I(L_\alpha) = C I_{in} \frac{\mu_{L_\alpha}(p.e.)f}{\mu(E_{in}) + \mu(L_\alpha)}(1 - \exp[-(\mu(E_{in}) + \mu(L_\alpha))D]) \quad \text{1a}$$

Eq. 1b shows the similar relationship for the $L_\beta$ peak.

$$I(L_\beta) = C I_{in} \frac{\mu_{L_\beta}(p.e.)f}{\mu(E_{in}) + \mu(L_\beta)}(1 - \exp[-(\mu(E_{in}) + \mu(L_\beta))D]) \quad \text{1b}$$

Eqs. 2a and 2b describe the situation shown in FIG. 1C in which the fluorescing radiation and the fluoresced radiation are absorbed by an outer layer (OL) of areal density $D_{outer}$. Geometrical factors have been omitted.

$$I(L_\alpha) = C I_{in} \frac{\mu_{L_\alpha}(p.e.)f}{\mu(E_{in}) + \mu(E_{L_\alpha})} \quad \text{2a}$$
$$(\exp[\mu_{OL}(E_{in}) + \mu_{OL}(L_\alpha)D_{outer})(1 - \exp[-(\mu(E_{in}) + \mu(L_\alpha)D_{Pb}])$$

$$I(L_\beta) = C I_{in} \frac{\mu_{L_\alpha}(p.e.)f}{\mu(E_{in}) + \mu(E_{L_\beta})} \quad \text{2b}$$
$$(\exp[\mu_{OL}(E_{in}) + \mu_{OL}(L_\beta)D_{outer})(1 - \exp[-(\mu(E_{in}) + \mu(L_\beta)D_{Pb}])$$

Eq. 3 is the ratio of Eq. 2b to Eq. 2a.

$$\frac{I(L_\beta)}{I(L_\alpha)} \cong \frac{\mu_{L_\beta}(p.e.)[\mu(E_{in}) + \mu(L_\alpha)]}{\mu_{L_\alpha}(p.e.)[\mu(E_{in}) + \mu(L_\beta)]} \frac{(1 - \exp[-(\mu(E_{in}) + \mu(L_\beta))D])}{(1 - \exp[-(\mu(E_{in}) + \mu(L_\alpha))D])} \quad 3)$$

In the limit in which the exponents in Eq. 3 are large, which in practice means that the areal density D of the matrix containing the sought-after element is large, Eqn. 3 simplifies to, $$\left[\frac{I(L_\beta)}{I(L_\alpha)}\right]_{D\to\infty} = \frac{\mu_{L_\beta}(p.e.)[\mu(E_{in}) + \mu(L_\alpha)]}{\mu_{L_\alpha}(p.e.)[\mu(E_{in}) + \mu(L_\beta)]}. \quad 4)$$

Eq. 4 has a maximum value for lead of about 1.3. The actual value will depend on geometrical factors that are specific to the XRF instrument used.

Figure 4:
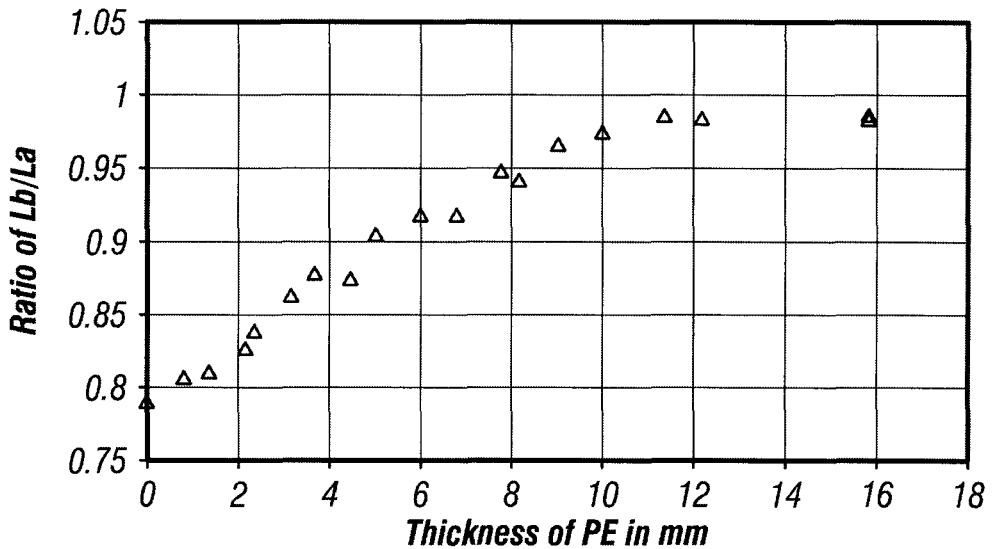
FIG. 4 is an empirical plot of the ratio of $L_\beta$ to $L_\alpha$ intensities for 805 ppm of lead in polyethylene, as a function of the thickness of the polyethylene.

FIG. 4 shows a calculated plot of the $L_\beta/L_\alpha$ vs. D obtained from Eq. 3 for a polyethylene object, a common toy material. The values used in the calculation are similar to those for other common plastics, including ABS, methacrylates and polypropylenes, as well as rubber compounds.

It should be noted that the calculations take into account the absorption of the exciting and de-exciting radiations but do not take into account the decrease in solid angle for elements at further distances from the front surface. Such efficiencies depend on specific design of the XRF instrument used The point is emphasized by FIG. 5, which shows an empirical determination of $L_\beta/L_\alpha$ for samples of polyethylene doped with 805 µg/g of Pb. The XRF instrument was the ThermoFisher Niton model XL3. The ratio saturates at a value of unity, rather than 1.2 because the detector is insensitive to radiations from deeper than a centimeter from the surface.

Three characteristics are worthy of particular note:
1. The ratio of $L_\beta/L_\alpha$ is a direct measure of the maximum thickness of the polyethylene from which the fluoresced L x-rays are observed.
2. When the exponents in Equation 3 are large, the ratio reaches the saturation value given in Equation 4. The saturation value is nearly independent of material. For example, $L_\beta/L_\alpha$=1.2, 1.3, and 1.25 for polyethylene, PVC, and copper, respectively.
3. In the limit when the exponents in Eq. 3 are very small, which is the case for paint, the ratio simplifies further and becomes independent of the thickness D, $$\left[\frac{I(L_\beta)}{I(L_\alpha)}\right]_{D\to 0} = \frac{\mu_{L_\beta}(p.e.)}{\mu_{L_\alpha}(p.e.)},\quad 5)$$

which is the ratio of the probabilities for generating the $L_\beta$ and $L_\alpha$ line by the fluorescing radiation. For lead, this ratio is close to 0.8.

In summary: If the lead is on the surface, the ratio R is a constant whose value is given to first approximation by Eq. 5 for a single monoenergetic fluorescing radiation. Since the experimental value of $R_{surface}$ depends on the relative efficiencies for detecting the L lines and may depend on the spectrum of input fluorescing radiation, the exact value, which should be determined empirically, will not be much different from 0.8.

On the other hand, if the lead is in the bulk material, the value of R will be greater than $R_{surface}$, (it is never less). The measured value of R determines the thickness D, in $g/cm^2$, from which the fluoresced L lines originate. The relationship between R and D, given in Equation 3 and shown in FIG. 4, is a guide since geometrical effects have not been included. Empirical calibrations, carried out at the factory, are necessary for each distinct XRF instrument model. FIG. 5 shows an empirical calibration for the ThermoFisher, NITON XL3 analyzer, whose detector is insensitive to radiations coming from more than a centimeter from the front face of the instrument. The ratio $L_\beta/L_\alpha$ saturates at a value close to unity for polyethylene.

The ratio, $L_\beta/L_\alpha$, thus determines whether the lead is on the surface or the bulk and allows the XRF instrument to automatically choose the proper algorithm for analysis. Specifically:
  If the ratio is in the range expected for surface lead, i.e. near the value of 0.8, then the so-called semi-empirical method, well known in the art, gives an accurate measure of the lead concentration in $\mu g/cm^2$.
  If the ratio is in the range expected for bulk lead, i.e. in the range from 0.9 to 1.4, then the well-known methods of fundamental parameters, or Compton normalization, can give an accurate measure of the lead concentration in $\mu g/g$.

The situation shown in FIG. 1C is distinct from either of the situations shown in FIGS. 1A and 1B, and its analysis method is also distinct. The lead in FIG. 1C is buried by some thickness of non-leaded material. There is no material containing lead at the surface. To fluoresce the buried lead, both the incoming excitation and the outgoing lead x-rays must pass through the outer layer and suffer absorption. The consequence is that the Eqs. 3, 4 and 5, which describe the $L_\beta/L_\alpha$ ratio for the situations in FIGS. 1a and 1b, become modified by the multiplication factor $\exp[(\mu_{OL}(L_\alpha)-\mu_{OL}(L_\beta))\,D_{OL}]$.

The value of this multiplier can be very large. The ratio, $L_\beta/L_\alpha$ can easily exceed the maximum value of about 1.4 for bulk lead. For example, a 10 mil thick PVC outer layer will increase the value of R by a factor of 1.4; a 20 mil coating will result in a ratio of $L_\beta/L_\alpha$ that exceeds 2. The sensitivity of the ratio $L_\beta/L_\alpha$ to the thickness of an outer layer, is the basis for automatically determining that observed lead is buried beneath material that does not contain lead.

The analytic method for determining the lead concentration when the lead is buried has been extensively discussed in the aforementioned Grodzins and Grodzins/Parsons patents. When the sample is made of unknown materials of unknown thickness, the Grodzins patents show that a quantitative measure of the lead concentration can be determined if the intensities of both the $L_\alpha$ and $L_\beta$ x-rays are measured. The method is based on measuring the ratio of the two intensities and using calibration standards, together with the absolute value of the intensity of one of the L lines, to determine the concentration in $\mu g/cm^2$.

The automatic selection of the appropriate analytic algorithm is summarized as follows.
  1. If $R=L_\beta/L_\alpha$ is at the minimum value then the lead is in a thin layer on the surface and its concentration, in $\mu g/cm^2$ can be determined by standard semi-empirical methods.
     a. R (lead) is ~0.8. The value depends slightly on the specific design of the XRF instrument.
  2. If $R_{max}>R>R_{min}$, then the lead is in the bulk and its concentration, in $\mu g/g$ can be determined by standard methods such as Fundamental Parameters or Compton Normalization.
     a. The range between $R_{min}$ and $R_{max}$ needs to be determined empirically since it depends on the geometrical design of the XRF instrument. For the ThermoFisher Niton XL3, the values are $R_{min}$=0.9 and $R_{max}$=1.4.
  3. If $R>R_{max}$ then the lead is buried and its concentration in $\mu g/g$ needs to be determined by the methods described in Grodzins and Grodzins/Parsons.

The specific values given for the automated decision are preferably determined by calibration measurements in the laboratory using known concentrations of lead in plastics of different thicknesses. These measurements will modify the constants in Eqs. 1 and 2 to correct for such effects as the reduction in the signal strengths as a function of the distance of the lead from the fluorescing source and the detector of the fluoresced radiation.

In alternative embodiments, the disclosed methods for determining the content of a specified elemental substance within a sample may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

We claim:

1. A method for determining the concentration of an element of interest in a sample by x-ray fluorescence, comprising:
    directing an x-ray excitation beam onto at least a portion of the sample to cause the sample to fluorescently emit x-rays at first and second energies characteristic of the element of interest;
    measuring the intensities of the fluorescently emitted x-rays;
    calculating a ratio R of the measured intensity of x-rays of the second characteristic energy to the measured intensity of x-rays of the first characteristic energy;
    automatically selecting a concentration calculation method from a plurality of available concentration calculation methods based on the value of R;
    calculating a concentration of the element of interest using the selected concentration calculation method; and
    outputting the concentration of the element of interest.

2. The method of claim 1, wherein the element of interest is lead, and the x-rays of the first and second characteristic energies respectively correspond to the $L_\alpha$ and $L_\beta$ lines of lead.

3. The method of claim 2, wherein the plurality of available concentration calculation methods includes a first method in which the lead concentration is calculated as an areal density, and a second method in which the lead concentration is calculated as a volumetric concentration.

4. The method of claim 3, wherein the first method is selected if the value of R is about 0.8, and the second method is selected if the value of R is greater than about 0.8.

5. The method of claim 3, wherein the plurality of concentration calculation methods further includes a third method in which the lead concentration is calculated as a volumetric concentration, and wherein the first method is selected if the value of R is about 0.8, the second method is selected if the value of R is greater than about 0.8 and less than a specified maximum $R_{max}$, and the third method is selected if the value of R is equal to or greater than $R_{max}$.

6. The method of claim 5, wherein $R_{max}$ is about 1.4.

7. An x-ray fluorescence (XRF) analyzer comprising:
    a source for generating an x-ray excitation beam to be directed onto a sample;
    a detector positioned to receive x-rays emitted from the sample, the emitted x-rays including fluorescently emitted x-rays at first and second energies characteristic of an element of interest, the detector responsively producing signals representative of the intensities of the fluorescently emitted x-rays;
    a signal processor, coupled to the detector and programmed with instructions for calculating a ratio R of a measured intensity of x-rays of the second characteristic energy to a measured intensity of x-rays of the first characteristic energy, automatically selecting a concentration calculation method from a plurality of available concentration calculation methods based on the value of R, and calculating a concentration of the element of interest using the selected concentration calculation method; and
    an output for presenting the calculated concentration of the element of interest.

* * * * *